(12) United States Patent
Bierman

(10) Patent No.: US 8,100,862 B2
(45) Date of Patent: Jan. 24, 2012

(54) INSERTION SITE PROTECTION DEVICE

(75) Inventor: Steve F. Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 1166 days.

(21) Appl. No.: 11/436,893

(22) Filed: May 17, 2006

(65) Prior Publication Data

US 2006/0264836 A1 Nov. 23, 2006

Related U.S. Application Data

(60) Provisional application No. 60/682,289, filed on May 18, 2005.

(51) Int. Cl.
*A61M 5/32* (2006.01)

(52) U.S. Cl. .......................................... 604/174; 604/180

(58) Field of Classification Search .................. 604/174, 604/180, 533; 128/847, 888, 200.26, DIG. 6
See application file for complete search history.

(56) References Cited

U.S. PATENT DOCUMENTS

| | | | |
|---|---|---|---|
| 3,046,984 A | 7/1962 | Eby | |
| 3,194,235 A | 7/1965 | Cooke | |
| 3,568,679 A * | 3/1971 | Reif | 604/180 |
| 3,901,226 A | 8/1975 | Scardenzan | |
| 4,082,094 A | 4/1978 | Dailey | |
| 4,129,128 A | 12/1978 | McFarlane | |
| D252,822 S | 9/1979 | McFarlane | |
| 4,193,174 A | 3/1980 | Stephens | |
| 4,224,937 A | 9/1980 | Gordon | |
| 4,250,880 A | 2/1981 | Gordon | |
| 4,484,913 A | 11/1984 | Swauger | |
| 4,516,968 A | 5/1985 | Marshall et al. | |
| 4,517,971 A | 5/1985 | Sorbonne | |
| 4,563,177 A | 1/1986 | Kamen | |
| 4,632,670 A | 12/1986 | Mueller | |
| 4,633,863 A | 1/1987 | Filips et al. | |
| 4,645,492 A | 2/1987 | Weeks | |
| 4,667,666 A | 5/1987 | Fryslie | |
| 4,711,636 A | 12/1987 | Bierman | |
| 4,852,844 A | 8/1989 | Villaveces | |
| 4,863,432 A | 9/1989 | Kvalo | |
| 4,898,587 A | 2/1990 | Mera | |
| 4,976,698 A | 12/1990 | Stokley | |
| 4,997,421 A | 3/1991 | Palsrok et al. | |
| 5,037,397 A | 8/1991 | Kalt et al. | |
| 5,074,847 A | 12/1991 | Greenwell et al. | |

(Continued)

FOREIGN PATENT DOCUMENTS

CA 1 311 977 12/1992

(Continued)

*Primary Examiner* — Nicholas D Lucchesi
*Assistant Examiner* — Rebecca E Eisenberg
(74) *Attorney, Agent, or Firm* — Knobbe Martens Olson & Bear, LLP

(57) ABSTRACT

A securement device holds a medical article such as a catheter hub or a connector fitting in position upon the body of a patient and at least inhibits distal, longitudinal movement of the medical article. The securement device includes a retainer and at least one anchor pad. The retainer includes an abutment wall and a slot. The slot has a labyrinth shape leading to a cradle part of the slot. At least a portion of the medical article is inserted into the cradle part through the slot. The abutment wall includes at least one abutment that abuts against a contact point or surface on the medical article to inhibit distal, longitudinal movement of the medical article.

22 Claims, 13 Drawing Sheets

U.S. PATENT DOCUMENTS

| | | |
|---|---|---|
| 5,116,324 A | 5/1992 | Brierley et al. |
| 5,137,519 A | 8/1992 | Littrell et al. |
| 5,192,273 A | 3/1993 | Bierman |
| 5,192,274 A | 3/1993 | Bierman |
| 5,215,532 A | 6/1993 | Atkinson |
| 5,230,350 A | 7/1993 | Fentress |
| 5,238,010 A | 8/1993 | Grabenkort et al. |
| 5,290,248 A | 3/1994 | Bierman et al. |
| D347,060 S | 5/1994 | Bierman |
| 5,314,411 A | 5/1994 | Bierman et al. |
| 5,328,487 A | 7/1994 | Starchevich |
| 5,354,282 A | 10/1994 | Bierman |
| 5,356,391 A | 10/1994 | Stewart |
| 5,370,627 A | 12/1994 | Conway |
| 5,395,344 A | 3/1995 | Beisang et al. |
| 5,413,120 A | 5/1995 | Grant |
| 5,413,562 A | 5/1995 | Swauger |
| D359,120 S | 6/1995 | Sallee et al. |
| 5,456,671 A | 10/1995 | Bierman |
| D364,922 S | 12/1995 | Bierman |
| D375,355 S | 11/1996 | Bierman |
| D375,356 S | 11/1996 | Bierman |
| 5,577,516 A | 11/1996 | Schaeffer |
| 5,578,013 A | 11/1996 | Bierman |
| D377,831 S | 2/1997 | Bierman |
| 5,605,546 A | 2/1997 | Wolzinger et al. |
| 5,681,290 A | 10/1997 | Alexander |
| 5,685,859 A | 11/1997 | Kornerup |
| 5,686,096 A | 11/1997 | Khan et al. |
| 5,690,616 A | 11/1997 | Mogg |
| 5,693,032 A | 12/1997 | Bierman |
| 5,702,371 A | 12/1997 | Bierman |
| 5,722,959 A | 3/1998 | Bierman |
| 5,728,053 A | 3/1998 | Calvert |
| 5,733,571 A | 3/1998 | Sackler |
| 5,800,402 A | 9/1998 | Bierman |
| 5,800,410 A | 9/1998 | Gawreluk |
| 5,810,781 A | 9/1998 | Bierman |
| D399,954 S | 10/1998 | Bierman |
| 5,827,239 A | 10/1998 | Dillon et al. |
| 5,833,666 A | 11/1998 | Davis et al. |
| 5,833,667 A | 11/1998 | Bierman |
| 5,855,591 A | 1/1999 | Bierman |
| 5,885,254 A | 3/1999 | Matyas |
| 5,897,519 A | 4/1999 | Shesol et al. |
| 6,050,934 A | 4/2000 | Mikhail et al. |
| D425,619 S | 5/2000 | Bierman |
| 6,096,943 A | 8/2000 | Maiwald |
| 6,099,509 A | 8/2000 | Brown et al. |
| 6,113,577 A | 9/2000 | Hakky et al. |
| 6,132,398 A | 10/2000 | Bierman |
| 6,132,399 A | 10/2000 | Shultz |
| 6,213,979 B1 | 4/2001 | Bierman |
| 6,224,571 B1 | 5/2001 | Bierman |
| 6,231,547 B1 | 5/2001 | O'Hara |
| 6,231,548 B1 | 5/2001 | Bassett |
| 6,241,697 B1 | 6/2001 | Augustine |
| 6,255,552 B1 | 7/2001 | Cummings et al. |
| 6,258,066 B1 | 7/2001 | Urich |
| 6,264,977 B1 | 7/2001 | Hoffmann |
| 6,290,676 B1 | 9/2001 | Bierman |
| 6,361,523 B1 | 3/2002 | Bierman |
| 6,375,639 B1 | 4/2002 | Duplessie |
| 6,413,240 B1 | 7/2002 | Bierman et al. |
| 6,428,515 B1 | 8/2002 | Bierman et al. |
| 6,436,073 B1 | 8/2002 | Teichert |
| 6,447,485 B2 | 9/2002 | Bierman |
| 6,447,486 B1 | 9/2002 | Tollini |
| 6,471,676 B1 | 10/2002 | DeLegge et al. |
| 6,482,183 B1 | 11/2002 | Pausch |
| 6,491,664 B2 | 12/2002 | Bierman |
| 6,500,154 B1 | 12/2002 | Hakky et al. |
| D469,530 S | 1/2003 | Gomez |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 6,626,890 B2 | 9/2003 | Nguyen et al. |
| D492,411 S | 6/2004 | Bierman |
| 6,770,055 B2 | 8/2004 | Bierman et al. |
| 6,809,230 B2 | 10/2004 | Hancock et al. |
| 6,827,706 B2 | 12/2004 | Tollini |
| 6,827,707 B2 | 12/2004 | Wright et al. |
| 6,834,652 B2 | 12/2004 | Altman |
| 6,855,135 B2 | 2/2005 | Lockwood et al. |
| 6,981,969 B2 | 1/2006 | Chavez et al. |
| 7,014,627 B2 | 3/2006 | Bierman |
| 7,070,580 B2 | 7/2006 | Nielsen |
| 7,090,660 B2 | 8/2006 | Roberts et al. |
| 2002/0068904 A1 | 6/2002 | Bierman et al. |
| 2002/0099360 A1 | 7/2002 | Bierman |
| 2003/0055382 A1 | 3/2003 | Schaeffer |
| 2003/0069529 A1 | 4/2003 | Augustine et al. |
| 2003/0229313 A1 | 12/2003 | Bierman |
| 2004/0111067 A1 | 6/2004 | Kirchhofer |
| 2004/0138624 A1 | 7/2004 | Bierman |
| 2004/0143220 A1 | 7/2004 | Worthley |
| 2004/0204685 A1 | 10/2004 | Wright et al. |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0084922 A1 * | 4/2006 | Botha ............................ 604/174 |
| 2006/0135944 A1 | 6/2006 | Bierman |
| 2006/0217669 A1 | 9/2006 | Botha |
| 2006/0247577 A1 * | 11/2006 | Wright ............................ 604/174 |
| 2006/0264836 A1 | 11/2006 | Bierman |
| 2006/0270995 A1 | 11/2006 | Bierman |
| 2009/0048563 A1 | 2/2009 | Ethelfeld et al. |

FOREIGN PATENT DOCUMENTS

| | | |
|---|---|---|
| CA | 1 318 824 | 6/1993 |
| EP | 0356683 | 3/2000 |
| WO | WO 94/21319 | 9/1994 |
| WO | WO 97/15337 | 5/1997 |
| WO | WO 99/55409 | 11/1999 |

* cited by examiner

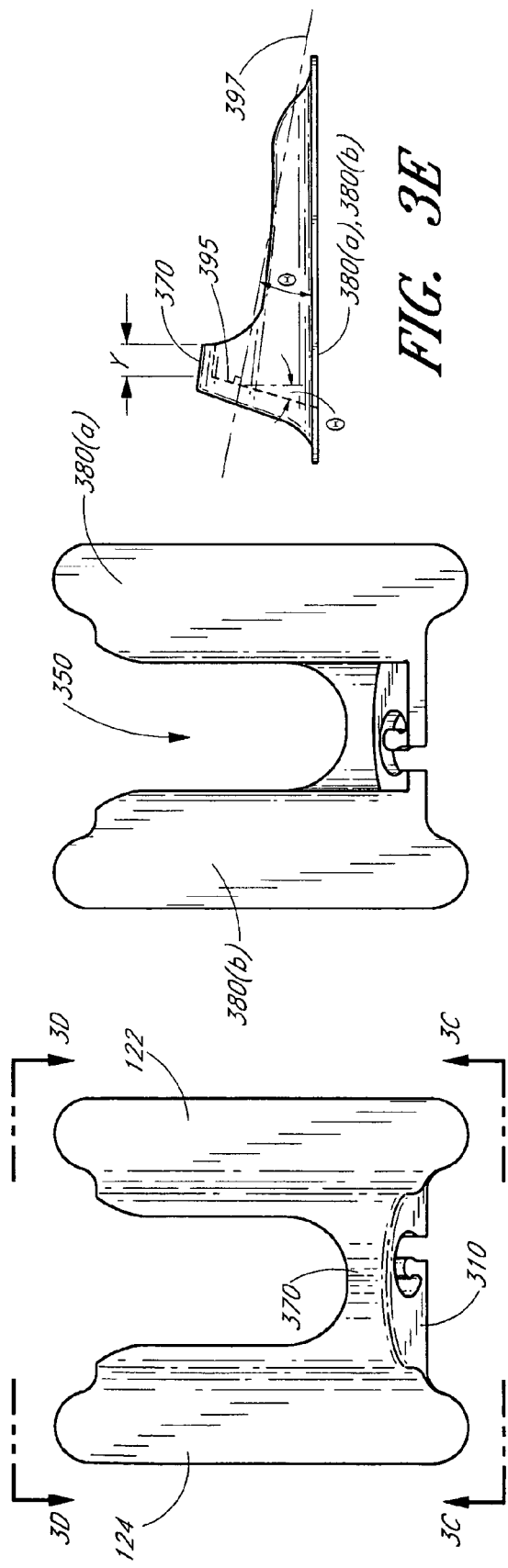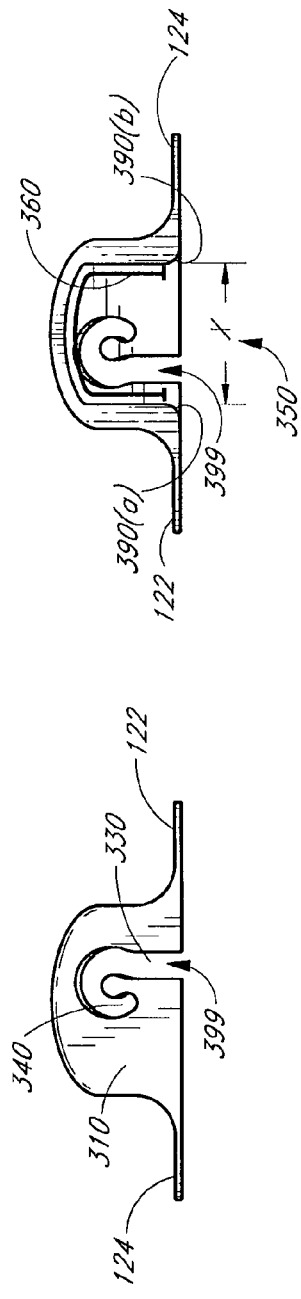

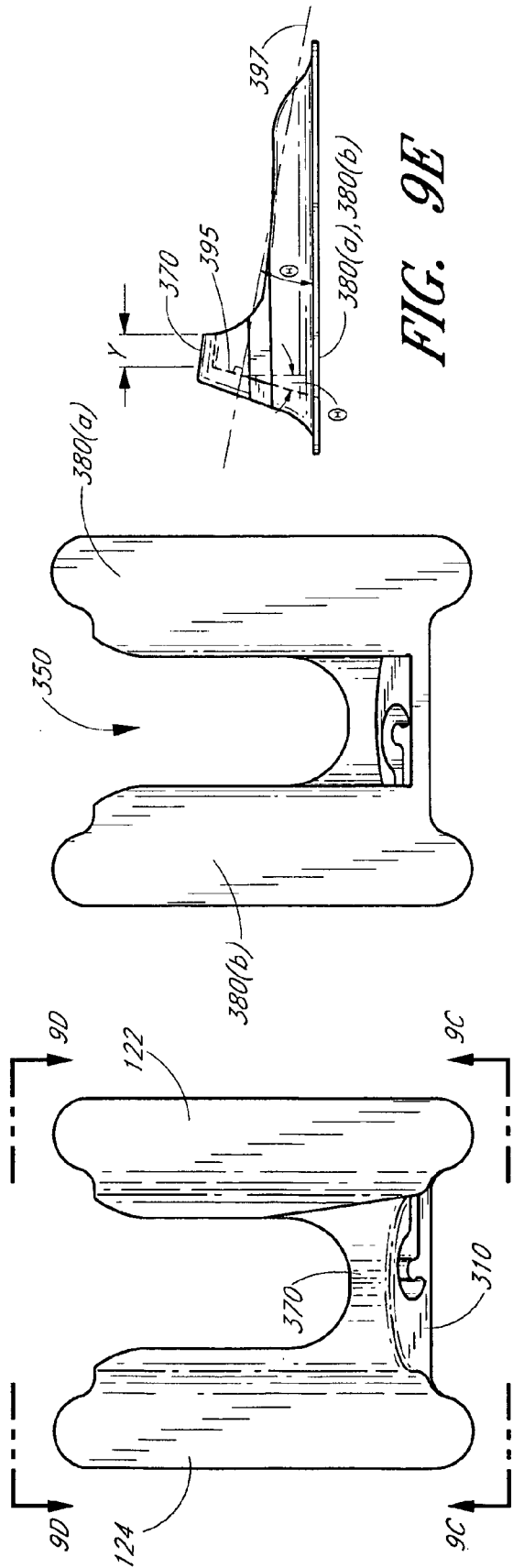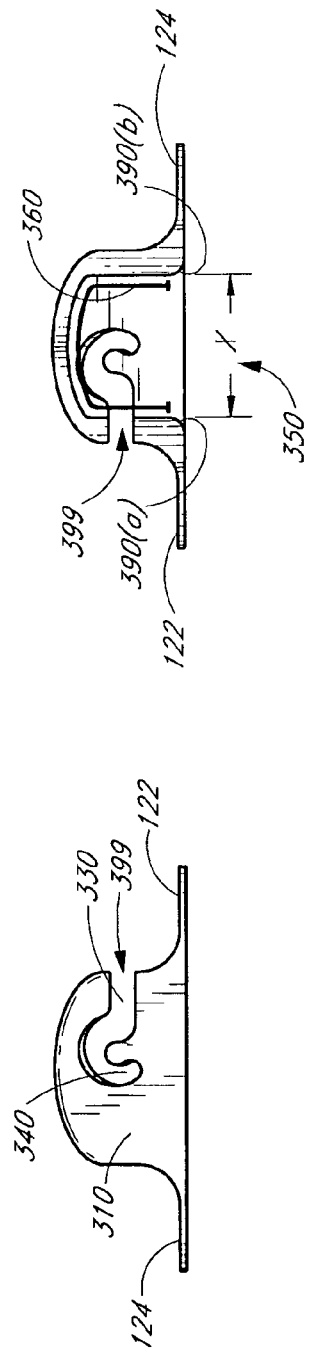

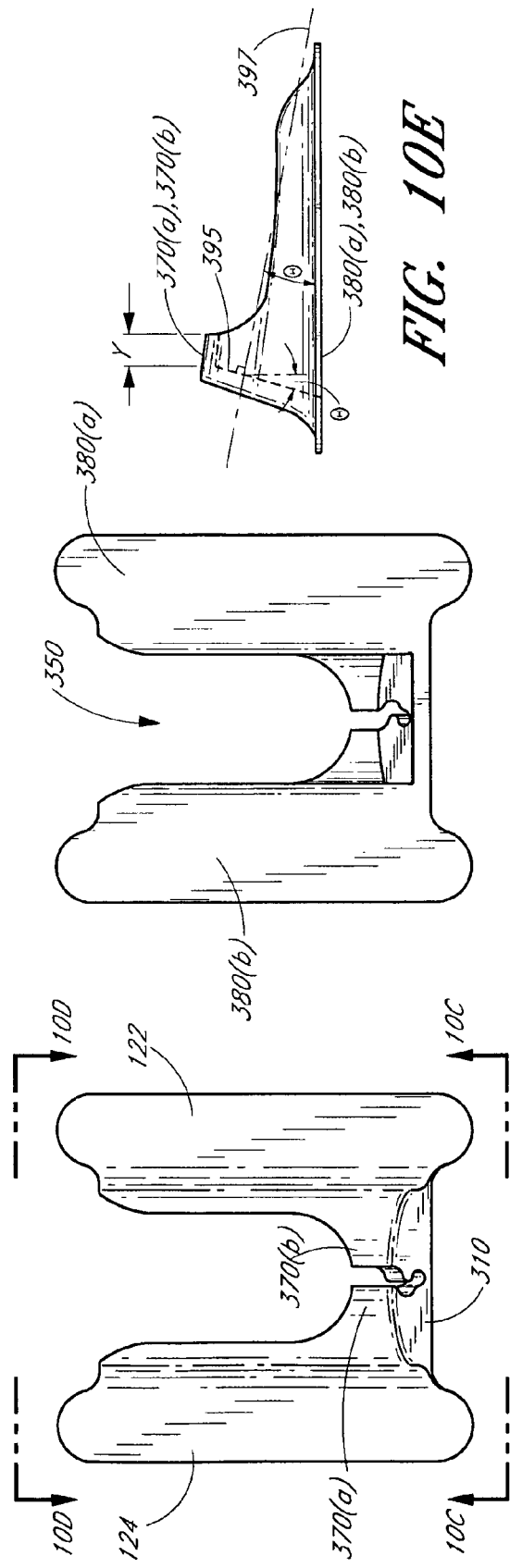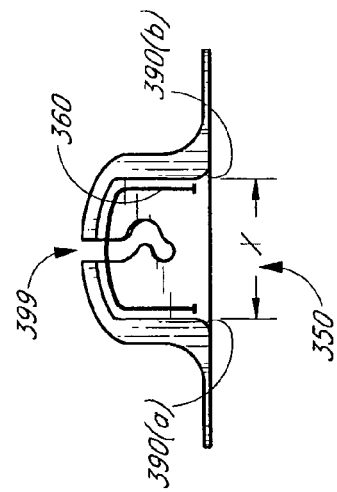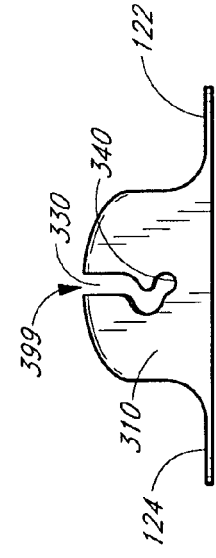

INSERTION SITE PROTECTION DEVICE

RELATED APPLICATIONS

This application claims priority under 35 U.S.C. §119(e) to U.S. Provisional Patent Application Ser. No. 60/682,289, filed May 18, 2005, and which is hereby expressly incorporated by reference in its entirety.

BACKGROUND OF THE INVENTION

1. Field of the Invention

This invention relates to an insertion site protection device used to attach a medical article to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, the primary retention method involves taping the catheter or medical line to the patient.

Securing a catheter with tape upon the patient has certain drawbacks. The use of tape as the primary retention method at the insertion site can retain dirt or other contaminant particles, potentially leading to infection of the patient. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for medical attendants.

For these reasons, a need exists for an improved way to secure catheters and medical lines to patients where the catheter can remain in place over an extended period of time without using tape as the primary retention method.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments," one will understand how the features of this invention provide several advantages over traditional catheter securement techniques.

One aspect of the present invention involves a medical line securement system that comprises a medical article having a longitudinal axis, at least one anchor pad including a lower adhesive surface configured to attach to a patient's skin, and a body member. The body member comprises an abutment wall extending generally normal to the longitudinal axis and a slot in the abutment wall. The slot starts at an access opening and includes a cradle portion. The slot is sized to pass at least a portion of the medical article between the access opening and the cradle portion. The body member further comprises a first support and a second support disposed on the underside of the body member and generally on opposite sides of the longitudinal axis. The first support and the second support extend generally along the longitudinal axis and at least one of the first and second supports attach to the at least one anchor pad. The body member further comprises a receiving space generally defined on a proximal side of the abutment wall and between the first and second supports. The receiving space is sized to receive at least a portion of the medical article.

Another aspect of the invention involves a retainer configured for use with a medical article. The retainer comprises at least one anchor pad that includes a lower adhesive surface configured to attach to a patient's skin and a body member. The body member comprises an abutment wall extending generally normal to the longitudinal axis and a slot. The slot has a labyrinth shape and extends between an access opening and a cradle portion. The slot is sized to pass the retained portion of the medical article therebetween. The access opening is disposed on the body member to allow at least ingress of the portion of the medical article into the slot. The body member further comprises a first support and a second support disposed on the underside of the body member and generally on opposite sides of the longitudinal axis. The first support and the second support extend generally along the longitudinal axis and are attached to the at least one anchor pad. The body member further comprises a receiving space generally disposed on a proximal side of the abutment wall and between the first and second supports. The receiving space is sized to receive at least a portion of the medical article.

An additional aspect of the invention involves a method of securing a medical article to a patient. The method comprises positioning an elongated medical article on a body of a patient and providing a retainer having an abutment wall and a slot. The abutment wall extends generally normal to a longitudinal axis of the medical article. At least a portion of the slot forms a cradle to hold at least a portion of the medical article away from the patient's skin when the portion of the medical article is secured within the cradle. The method further comprises inserting the portion of the medical article into the slot through an opening formed on a side of the retainer and guiding the medical line through the slot and into the cradle so as to position the medical article in the retainer. The method further comprises adhering the retainer relative to a patient's skin.

BRIEF DESCRIPTION OF THE DRAWINGS

These and other features, aspects, and advantages of the present invention will now be described in connection with preferred embodiments of the invention, in reference to the accompanying drawings. The illustrated embodiments, however, are merely examples and are not intended to limit the invention.

FIG. 3B is a top plan view of the retainer.

FIG. 3C is a front side view of the retainer and illustrates an inverted, hook-shaped slot that receives a section of a medical article.

FIG. 3D is a back side view of the retainer and illustrates a u-shaped channel or receiving space that receives a section of the medical article.

FIG. 3E is a side view of the retainer.

FIG. 3F is a bottom plan view of the retainer.

FIG. 9B is a top plan view of the retainer of FIG. 9A.

FIG. 9C is a front side view of the retainer of FIG. 9A and illustrates a horizontal, hook-shaped slot that receives a section of a medical article.

FIG. 9D is a back side view of the retainer of FIG. 9A and illustrates a u-shaped channel that receive a section of the medical article.

FIG. 9E is a side view of the retainer of FIG. 9A.

FIG. 9F is a bottom plan view of the retainer of FIG. 9A.

FIG. 10B is a top plan view of an additional embodiment of the retainer.

FIG. 10C is a front side view of an additional embodiment of the retainer and illustrates a hook-shaped slot that receives a section of a medical article.

FIG. 10D is a back side view of an additional embodiment of the retainer and illustrates a u-shaped channel that receive a section of the medical article.

FIG. 10E is a side view of an additional embodiment of the retainer.

FIG. 10F is a bottom plan view of an additional embodiment of the retainer.

DETAILED DESCRIPTION OF THE PREFERRED EMBODIMENTS

The following description and figures describing the preferred embodiments are made to demonstrate various configurations of possible systems in accordance with the invention. The embodiments illustrated are shown in use with an exemplary connector fitting having a spin nut for connection to a catheter adaptor. This is not intended to limit the disclosed concepts to the specified embodiments or to usage with the illustrated connector only. In addition, various systems will be described in the context of an exemplary insertion site protection device incorporating the described systems and techniques. The techniques described are neither limited to any particular type of insertion site protection device, nor to the securement of any particular type of medical article for every described aspect herein.

To assist in the description of these components of the anchoring system (see FIG. 1) the following coordinate terms are used. A "longitudinal axis" is generally parallel to the portion of the connector fitting or other medical article retained by the insertion site protection system, as well as parallel to the axis of the cradle portion of the retainer. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present insertion site protection system, are used consistently with the description of the exemplary applications. Thus, proximal and distal are used in reference to the center of the patient's body. The terms "upper," "lower," "top," "bottom," and the like, which also are used to describe the present insertion site protection system, are used in reference to the illustrated orientation of the embodiment.

To facilitate a complete understanding of the invention, the remainder of the detailed description describes the invention with reference to the figures, wherein like elements are referenced with like numerals throughout the description.

Overview

Figure 1:
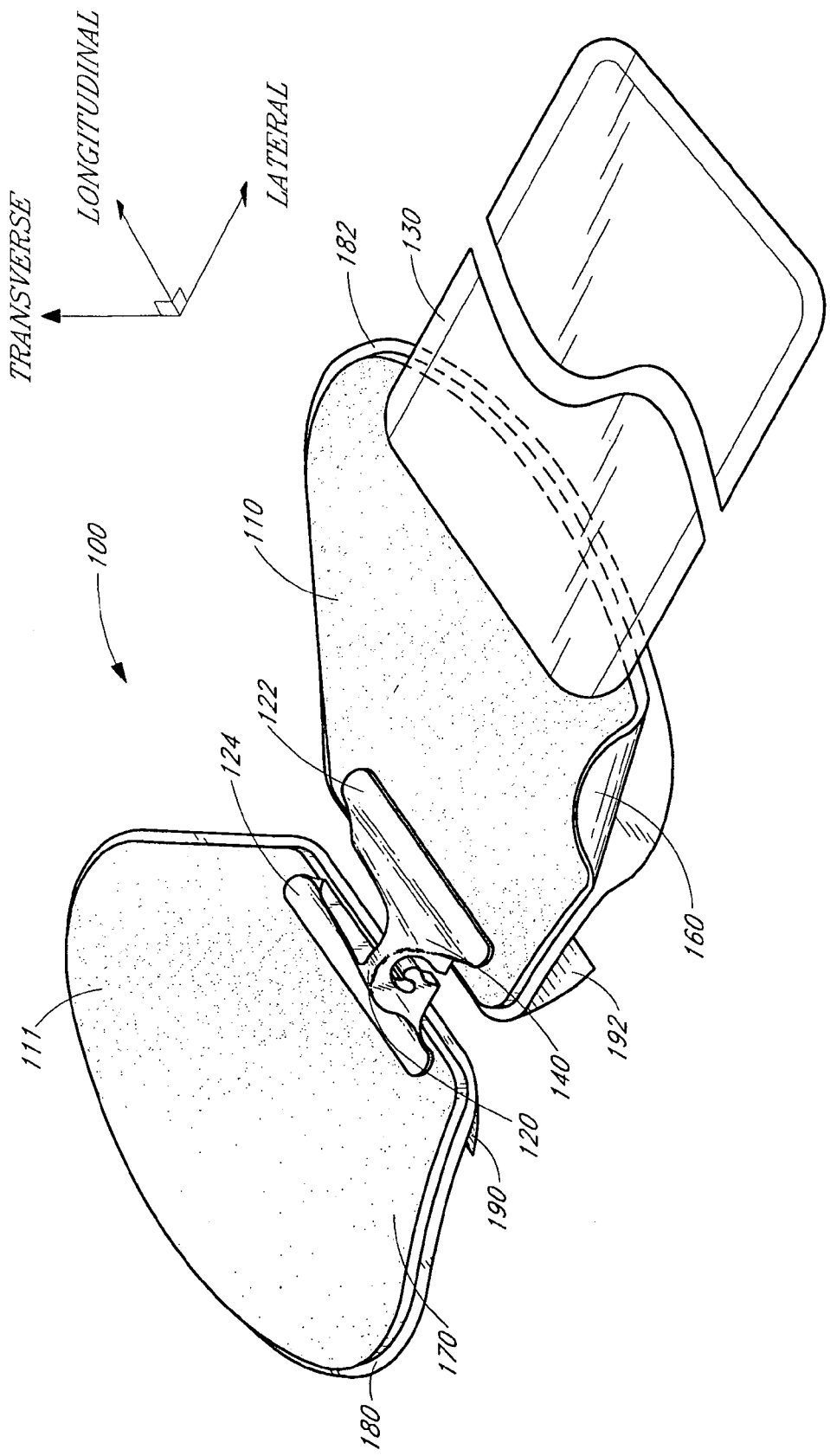
FIG. 1 is a perspective view of the insertion site protection device configured in accordance with a preferred embodiment of the present invention.
Figure 2:
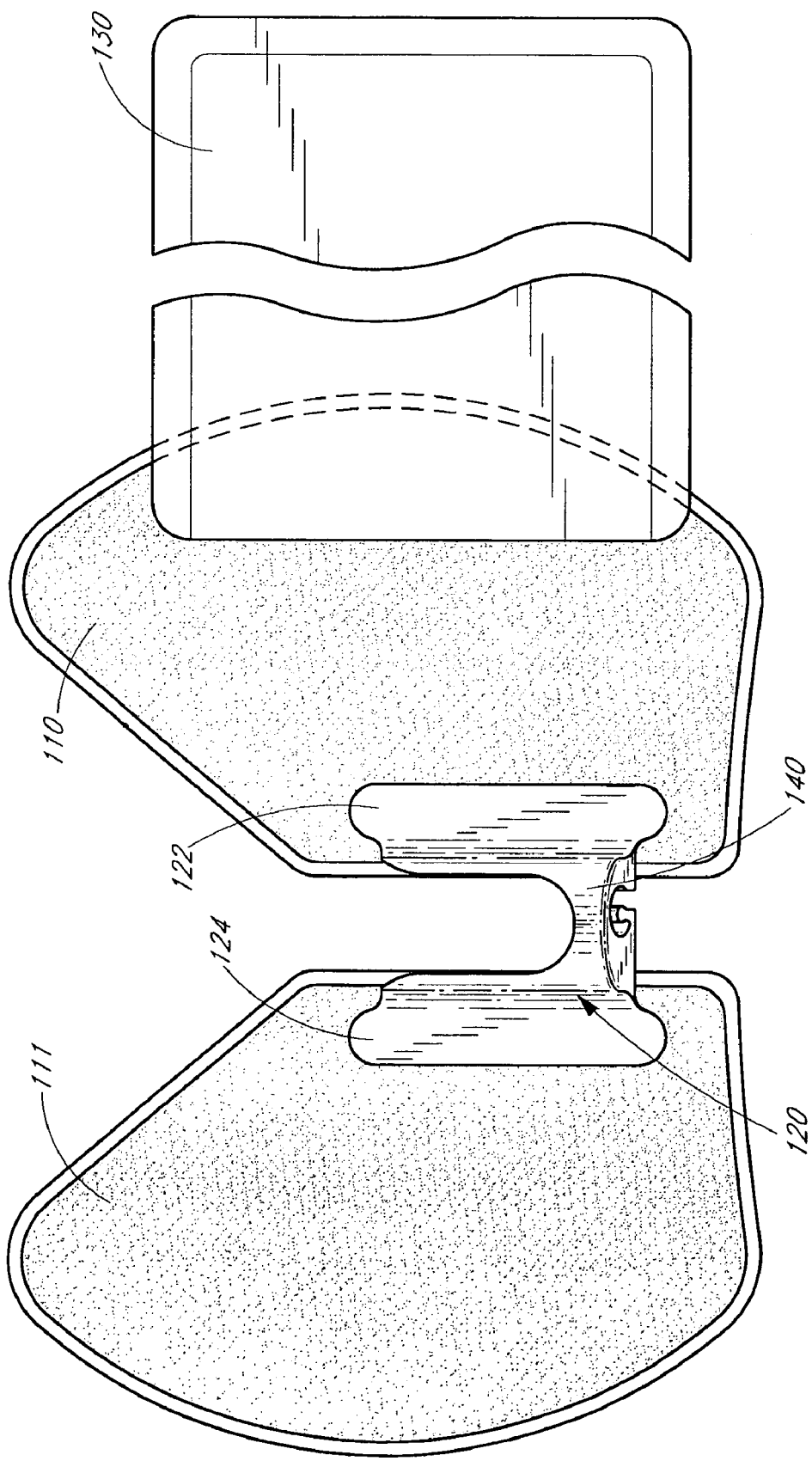
FIG. 2 is a top plan view of the insertion site protection device of FIG. 1 that includes a retainer and anchor pads with integral cover tape.

FIG. 1 is a perspective view of an insertion site protection device 100 configured in accordance with an embodiment of the present invention. FIG. 2 is a top plan view of the insertion site protection device 100 of FIG. 1. As shown in FIGS. 1 and 2, the described embodiment comprises an insertion site protection device 100 having three main components: anchor pads 110, 111 and a retainer 120. The retainer 120 comprises mounting wings 122, 124 which extend in lateral directions away from a body member 140. Bottom surfaces of the mounting wings 122, 124 attach the retainer 120 to the anchor pads 110, 111, respectively. An adhesive disposed upon the bottom surfaces of the anchor pads 110, 111 secures the anchor pads 110, 111 to the skin of the patient. In this way, the retainer 120 secures the medical article to the patient.

In other preferred embodiments, the insertion site protection device can include a single anchor pad 110, 111 which attaches to both mounting wings 122, 124. In these other embodiments as explained below, an access opening into the retainer 120 may be located on a side or top of the retainer for ingress of the medical article into the retainer 120.

The mounting wings 122, 124 may be fabricated integral to, or separate from, the body member 140. If fabricated integral with the body member 140, the body member 140 and mounting wings 122, 124 together form a unitary retainer 120. Alternatively, if the mounting wings 122, 124 are separately fabricated, each mounting wing 122, 124 is attached to the body member 140. The integral or attached mounting wings 122, 124 of the retainer 120 are secured to the anchor pads 110, 111 during fabrication of the insertion site protection device 100. In this way, the healthcare provider receives the assembled insertion site protection device 100 illustrated in FIG. 1. As noted above, the insertion site protection device 100 can form a component of a catheterization system or kit that also includes one or more medical articles, such as connector fittings, catheters, catheter adaptors, fluid supply lines, or other articles suitable for securement via the anchor pads 110, 111 and retainer 120. For example, the insertion site protection device 100 may secure a connector fitting with or without an attached medical line.

Figure 3A:
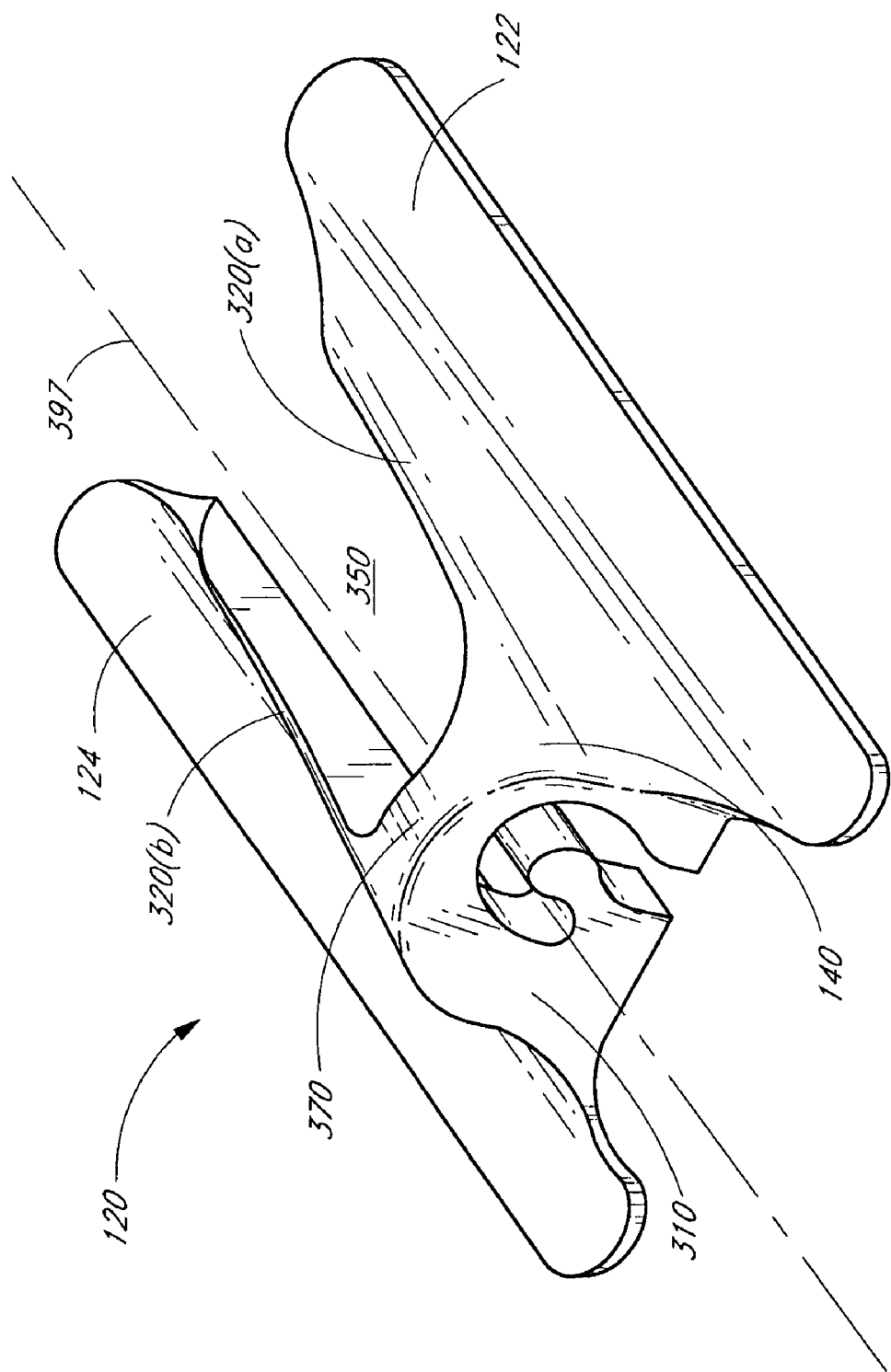
FIG. 3A is a perspective view of the retainer from FIG. 2.

FIG. 3A is a perspective view of the retainer 120 of FIG. 2. FIG. 3B is a top plan view of the retainer 120 of FIG. 2. FIG. 3C is a front side view of the retainer 120 and illustrates an inverted, hook-shaped slot 330 that receives a section of a medical article. As illustrated in FIGS. 3A, 3B, and 3C, the body member 140 comprises an abutment wall 310 and supports 320(a), 320(b) which extend proximally in a longitudinal direction therefrom. The body member 140 may additionally comprise a web 370, which unites the supports 320(a), 320(b) at their distal ends and forms an inverted channel 360 or receiving space (see FIG. 3D).

A lower opening 350, which is located between the mounting wings 122, 124 of the retainer 120, receives the medical article. The medical article is inserted between the anchor pads 110, 111 (see FIGS. 1 and 2) and up through the opening 350 such that at least a portion of the medical article is located in the channel 360 or receiving space (see FIG. 3D). For some embodiments of the retainer 120 disclosed herein, the medical article is inserted in a downward, transverse direction or in a lateral direction when installing the medical article in the retainer 120.

In the illustrated embodiment, the channel 360 is formed between the web 370 of the body member 140 and distal portions of the supports 320(a), 320(b). The walls of the channel 360 and/or the web 370 limit movement of the medical article when the insertion site protection device 100 is attached to the patient.

Before, after, or contemporaneous with inserting the medical article into the opening 350, a portion of the medical article is upwardly inserted through an access opening 399 and into the hook-shaped slot 330. A medical line portion of the medical article is inserted into the slot 330. The slot 330 may be sized to receive other portions of the medical article. For example, the slot 330 could be sized to receive a connector body of the medical article.

The slot 330 is located in the abutment wall 310 of the body member 140. In other embodiments, the slot 330 is located in the body member 140 but separate from the abutment wall 310. For example, the body member 140 may have an abutment wall 310 configured to abut a contact surface of the medical article so as to inhibit movement of the medical article in at least one longitudinal direction and a wall separate from the abutment wall 310 that has the slot 330.

The slot 330 guides the medical article between the access opening 399 in the slot 330 and the cradle portion 340 until the medical article comes to rest in the cradle portion 340. The cradle portion 340 may be located at the terminus of the slot 330 or at an intermediate location along the slot 330. The hook-shaped slot 330 in the illustrated embodiment has a labyrinth shape between the access opening 399 and the cradle portion 340. The labyrinth shaped slot 330 suitably does not obstruct or occlude fluid flowing through the retained portion of the medical article.

Once in the cradle portion 340, the medical article is inhibited from moving in a transverse and downward direction by the shape of the slot 330. The section of the medical line is further inhibited from moving in a lateral direction by the walls of the curved slot 360. Longitudinal movement of the medical article in a distal direction is inhibited by contact between the abutment wall 310 and a distal surface or protuberance of the medical article.

FIG. 3D is a back side view of the retainer 120 and illustrates the channel 360, a portion of which has an inverted U-shape. The channel 360 is located on the proximal side of the abutment wall 310 and receives at least a portion of the medical article (e.g., the catheter, adaptor, or connector fitting). The medical article, such as a connector fitting for a catheter, is inhibited from moving longitudinally in a distal direction by the abutment wall 310. Additionally, features of the retainer 120, for example, the supports 320(a), 320(b) and the web 370, can further arrest motion of the medical article in lateral and transverse directions, respectively. For example, a dimension X (see FIG. 3D), measured between the supports 320(a), 320(b), may be selected to equal or slightly exceed a maximum size (e.g., diameter) of the portion of the medical article to be retained. Lateral motion of the medical article may be reduced by decreasing X such that X is closer to the actual size of the retained section of the medical article. The channel 360 can have a non-uniform width along the longitudinal axis and narrow to dimension X at one or more longitudinal locations along the longitudinal axis. In the embodiment illustrated in FIG. 3D, dimension X extends for the length of the opening 350 along the longitudinal axis.

The retained medical article can include one or more side extending members. Exemplary side extending members include, for example, but without limitation, spin nuts, rings, side branches and T-parts. Depending on the relative longitudinal lengths of the retainer 120 and the medical article, the radially extending member of the medical article may be disposed along the longitudinal axis between the supports 320(a), 320(b) or beyond the ends of the supports 320(a), 320(b) in a proximal direction when the medical article is located within the retainer 120. For medical articles that include one or more side extending members located between the supports 320(a), 320(b), the maximum diameter of the medical article is measured at the location of the radially extending member. In such a case, the dimension X is selected to equal or exceed the diameter of the spin nut or other side extending structure of the medical article that will lie between the supports 320(a), 320(b). Additionally, the supports 320(a), 320(b) can incorporate one or more lateral side grooves or openings for receiving the spin nut or side extending member when the medical article is inserted into the retainer 120. Once the medical article is inserted into the retainer 120, the supports 320(a), 320(b) can substantially inhibit lateral movement of the retained portion of the medical article.

FIG. 3E is a side view of the retainer 120. The web 370 of the retainer 120 may inhibit motion of the retained portion of the medical article in a transverse direction. The dimension Y is the length of the web 370 measured in a generally longitudinal direction. In some applications it may be advantageous to size dimension Y for the web 370 to assist in inhibiting transverse movement of the retained medical article. Extending the length of dimension Y can decrease the transverse movement of the retained medical article and inhibit pivoting of the retained medical article.

FIG. 3F is a bottom plan view of the retainer 120 and illustrates base surfaces 380(a), 380(b). The base surfaces 380(a), 380(b) are secured to the anchor pads 110, 111.

When the connector fitting is properly positioned in the retainer 120 (such that a distal surface or protuberance of the connector fitting contacts the abutment wall 310), the abutment wall 310 inhibits longitudinal motion of the medical article and medical line in a distal direction. Additionally, a side extending portion of the medical article can be captured in the channel 360 between the supports 320(a), 320(b) to inhibit lateral motion of the medical article and attached medical line.

Anchor Pad

As shown in FIGS. 1 and 2, the retainer 120 comprises mounting wings 122, 124. During fabrication of the insertion site protection device 100, the base surfaces 380(a), 380(b) of the mounting wings 122, 124 are attached to the anchor pads 110, 111. The anchor pads 110, 111 desirably comprise a laminate structure with an upper foam layer (e.g., closed-cell polyethylene foam), and a lower adhesive layer. The lower adhesive layer constitutes the lower surface 160 of the anchor pads. The lower surface desirably is a medical-grade adhesive and can be either diaphoretic or nondiaphoretic, depending upon the particular application. Such foam with an adhesive layer is available commercially from Avery Dennison of Painsville, Ohio. The anchor pads 110, 111 can include suture holes in addition to the adhesive layer to further secure the anchor pads to the patient's skin.

Alternatively, a hydrocolloid adhesive can advantageously be used upon the anchor pads 110, 111 for attaching the anchor pads to the skin of the patient. The hydrocolloid adhesive can be used either alone or in combination with another medical grade adhesive (e.g., in combination with the adhesive available from Avery Dennison). The hydrocolloid adhesive has less of a tendency to excoriate the skin of a patient when removed. This can be particularly important for patients whose skin is more sensitive or fragile, such as those with a collagen deficiency or other skin related condition.

A surface of the upper foam layer constitutes an upper surface 170 of the anchor pads. Corona-treating the foam with a low electric charge can roughen the upper surface. The roughened or porous upper surface can improve the quality of the adhesive joint (which is described below) between the mounting wings 122, 124 and the anchor pads 110, 111. In the alternative, the flexible anchor pads can comprise a medical-grade adhesive lower layer, an inner foam layer and an upper paper or other woven or nonwoven cloth layer.

Two removable paper or plastic release liners 180, 182 desirably cover the adhesive bottom surfaces 160 of the anchor pads 110, 111 before use. The liners 180, 182 suitably resist tearing to ease attachment of the pad to a patient's skin.

Each liner 180, 182 further comprises a folded over portion to define a pull tab 190, 192. The pull tabs 190, 192 facilitate removal of the liners 180, 182 from the adhesive lower surface 160 of each anchor pad. A healthcare provider uses the pull tab 190, 192 by grasping and pulling on it so that the liner 180, 182 is separated from the lower surface 160. The pull tab 190, 192 overcomes any requirement that the healthcare provider pick at a corner edge or other segment of the liner in order to separate the liner from the adhesive layer. The pull tab 190, 192 of course can be designed in a variety of configurations. The pull tabs 190, 192 illustrated in FIG. 1 are located along lateral ends of the anchor pads 110, 111 and adjacent to the body member 140 of the retainer 120. The pull tab 190, 192 can be located along center lines of the anchor pads 110, 111; or alternatively, each pull tab can be located along any line of the anchor pad in order to ease the application of the anchor pad onto the patient's skin at a specific site. For example, an area of a patient's skin with an abrupt bend, such as at a joint, can require that the pull tab 190, 192 be aligned toward one of the lateral ends of the anchor pad rather than along the center line.

At least one of the anchor pads 110, 111 may further comprise a cover tape 130. The anchor pad 110 of the insertion site protection device 100 illustrated in FIG. 1 comprises the cover tape 130. Alternatively, the anchor pad 111 can comprise the cover tape 130 or both anchor pads 110, 111 can comprise the cover tape.

The cover tape 130 has an adhesive surface. As illustrated in FIGS. 1 and 2, a portion of the perimeter of the cover tape 130 is fixedly attached to one of the lateral ends of the anchor pad 110. After the anchor pads 110, 111 of the insertion site protection device 100 are attached to the skin of the patient, the cover tape 130 is wrapped over the insertion site protection device 100 and adhered to at least portions of the exposed surfaces of the anchor pads 110, 111, the retained medical article, and the retainer 120. The cover tape 130 and the anchor pads 110, 111 form a clamshell around the medical article and the retainer 120. In this way, the clamshell forms a sterile environment around the retained medical article which reduces the chance for infection and enhances healing. The length of the cover tape 130 is selected so that when the cover tape 130 is pulled in a lateral direction across the retainer 120, the cover tape 130 covers at least a portion of the insertion site protection device 100. An exemplary material for the cover tape 130 is Tegaderm transparent dressing which is available from 3M.

The anchor pads 110, 111 are disposed relative to the retainer 120 such that the tip of the catheter hub extends beyond the front edge of the anchor pads 110, 111 when the medical article is properly inserted within the retainer 120 and the connector fitting abuts against the wall 310. Although only a single shape of anchor pad and cover tape are illustrated in FIGS. 1 and 2, those of skill in the art will recognize that a variety of shapes can be used in various circumstances in order to most effectively attach the insertion site protection device to a patient.

Retainer

With reference now to FIGS. 3A through 3F, further descriptions of this embodiment will now be described. The retainer 120 can include a generally rigid structure (at least in comparison to foam or tape). The retainer 120, however, suitably is somewhat flexible in nature, due both in part to its structure and to the material used to form the retainer 120. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like.

The retainer 120 may be formed by injection molding using polyethylene or polypropylene material. However, other materials can be utilized, and the retainer can be non-unitary. For example, the abutment wall 310 portion of the retainer 120 and/or the mounting wings 122, 124 can be non-unitary. The web 370 of the retainer 120 can be clear or transparent to facilitate alignment of the retainer 120 with the connector fitting or other medical article during installation.

In the illustrated embodiment, the abutment wall 310 is integrally formed to comprise a unitary body member 140. This can be accomplished in any of a variety of ways well known to those skilled in the art. For instance, the entire retainer can be injection molded in order to reduce fabrication costs. The abutment wall 310 and the remaining portion of the body member 140, however, can also be formed separately and then coupled together. Additionally, the abutment wall 310 and remaining portion of the body member 140 can have other forms and can have other orientations relative to one another.

As can be seen in FIGS. 3B, 3E, and 3F, the body member 140 may have a generally forked shape with an opening above the channel 360. The prongs of the body member body 140 are the supports 320(a), 320(b). The inverted channel 360 is defined between the supports 320(a), 320(b) and extends from a proximal side of the abutment wall 310 and in a generally longitudinal direction. In the illustrated embodiment, the inverted channel 360 or receiving space is open from above to allow the healthcare provider to monitor the condition of the insertion site.

The lower opening 350 has generally parallel sides and receives a first portion of the medical article. The access opening 399 into the slot 330 receives a second portion of the medical article. Preferably, the second portion of the medical article is a medical line. Before installing the medical article into the retainer 120, the retainer 120 may be shifted in a distal direction relative to the medical article so that the lower opening 350 and the access opening 399 are aligned with a medical line portion of the medical article. After passing the medical line through the lower opening 350 and the access opening 399, the retainer 120 is slid in a proximal direction relative to the medical article until a contact surface of the medical article abuts the abutment wall 310.

The lower opening 350 may include contouring along its periphery in order to guide the first portion of the medical article into the retainer 120. In the embodiment shown in FIG. 3D, chamfered surfaces 390(a), 390(b) are formed where the inner surfaces of the supports 320(a), 320(b) connect to the base surfaces 380(a), 380(b) of the mounting wings 122, 124.

The base surfaces 380(a), 380(b) can be angled in the longitudinal direction. Angle theta (See FIG. 3E) may be selected to align an axis 397 through the cradle portion 340 of the hook-shaped slot 330 of the retainer so as to achieve a desired incident angle with which the medical article is to contact the skin of the patient. A variety of different angles can be used, ranging from 0° to 45°, and more suitably from 5° to 25°. For instance, for the securement of arterial catheters, it is desirable for the angle of incidence of the catheter to the skin of the patient to be about 12.5°. For the securement of intravenous catheters, it is desirable for the angle of incident of the catheter to the skin of the patient to be about 7°. By disposing the base surfaces 380(a), 380(b) of the retainer 120 at the desired angle relative to the wall 310, which will depend upon the particular securement application (e.g., securing an arterial catheter, an intravenous catheter, etc.), the proper angle of incidence for a catheter can be maintained.

While not illustrated, the base surfaces 380(a), 380(b) of the mounting wings 122, 124 (see FIGS. 1 and 2) of the retainer 120 can have a concave curved shape when viewed from the front side. In addition or in the alternative, the base surfaces can be skewed relative to each other so as to be inclined upward toward the center of the retainer. The amount and radius of curvature can be varied depending on the expected location of usage or application of the insertion site protection device 100. It will be appreciated that many common sites for insertion of medical lines which require securement will be located on anatomical regions exhibiting convex curvature, such as a dorsal side of a hand, a arm, a leg, a shoulder, etc. By providing a concave bottom profile to the retainer 120, the retainer will rock less once placed upon the patient via the anchor pads 110, 111.

The retainer 120 is designed such that the cradle portion 340, via a retained portion of the medical article, lifts/holds at least a portion of the medical article away from the skin of the patient.

A hook-shaped slot 330 extends from the access opening 399 into the abutment wall 310. The slot 330 may terminate at the cradle portion 340. The access opening 399 receives a portion or length of the medical article and thereby guides the medical article into the slot 330. The slot 330 guides the medical article to the cradle portion 340.

The cradle portion 340 is configured to support the received portion of the medical article. In the illustrated embodiment (see FIGS. 3A through 3F), the cradle portion 340 of the hook-shaped slot 330 has a generally semi-circular cross-sectional shape of constant radius along its longitudinal length. The size, for example, the radius of the cradle portion 340 can be chosen to match or approximate the size of various standard medical lines. By matching the size of the cradle portion 340 to the external radius of the retained medical article portion, a more effective securement may be achieved.

Although the cradle portion 340 can be formed in various shapes depending upon the desired application (i.e., depending upon a diameter of the medical article portion to be retained in the cradle portion 340), the cradle portion 340 desirably has a sufficient length in the longitudinal direction to provide some stability to the attached connector fitting, adaptor, or other medical article. Additionally, once the medical article is installed in the retainer 120, the healthcare provider may move the retainer 120 in the proximal direction relative to the medical article so that the proximal surface of the abutment wall 310 contacts a distal surface or protuberance of the medical article to further enhance the stability of the medical article. That is, when the cradle portion 340 receives a sufficient length of the medical article and the medical article abuts the abutment wall 310, movement of the medical article in the lateral, distal longitudinal, and transverse directions is reduced (i.e., to inhibit yaw, pitch and axial movement of the medical article).

The axis 397 of the cradle portion 340 suitably lies perpendicular to the proximal side of the abutment wall 310, and may also lie parallel to a plane through the web 370 of the retainer 120. Although this configuration can be advantageous for securing particular medical articles, those of skill in the art will recognize that the axis 397 through the cradle portion 340 can be disposed at an angle relative to the upper surface of the retainer 120 for particular applications. For instance, angling the axis 397 relative to the upper surface of the retainer 120 can create the desired angle between the medical article and the patient. In such cases, the upper surface of the web 370 could remain roughly parallel to the surface of the anchor pad 110 while the inner surface of the web 370 could be skew relative to the surface of the anchor pad 110.

During fabrication of the insertion site protection device 100, the retainer 120 is attached to the upper surface 170 of the anchor pads 110, 111 via the base surfaces of the mounting wings 122, 124, as is shown in FIGS. 1 and 2. The retainer 120 is desirably secured to the upper surface of the pad by a solvent bond adhesive, such as cyanoacrylate or other bonding material. One such adhesive is available commercially as Part No. 4693 from 3M.

Figure 6:
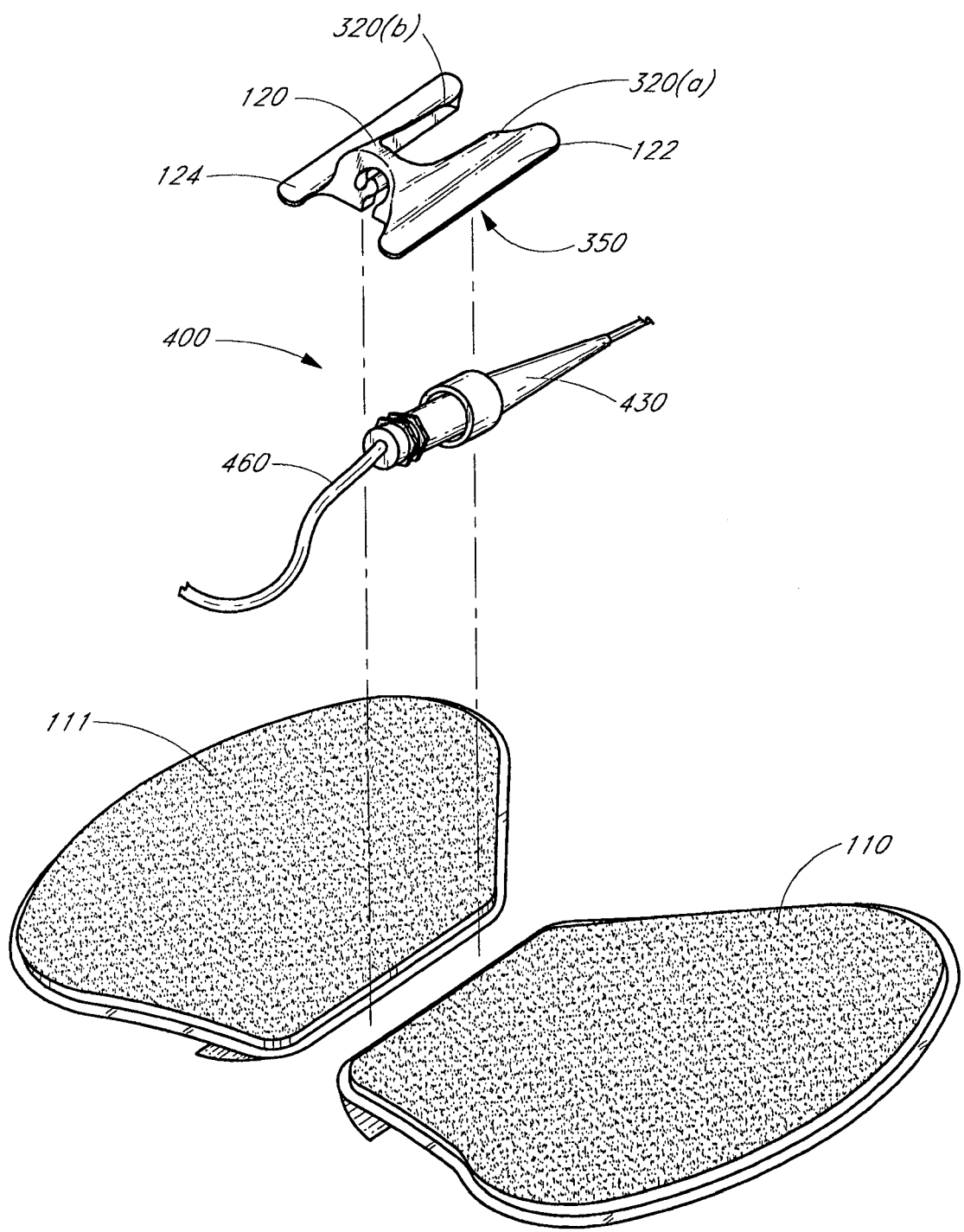
FIG. 6 is an exploded, perspective view of the connector fitting secured to the catheter hub of FIG. 4, the connector fitting aligned with the anchor pads and the retainer of FIG. 2.
Figure 7:
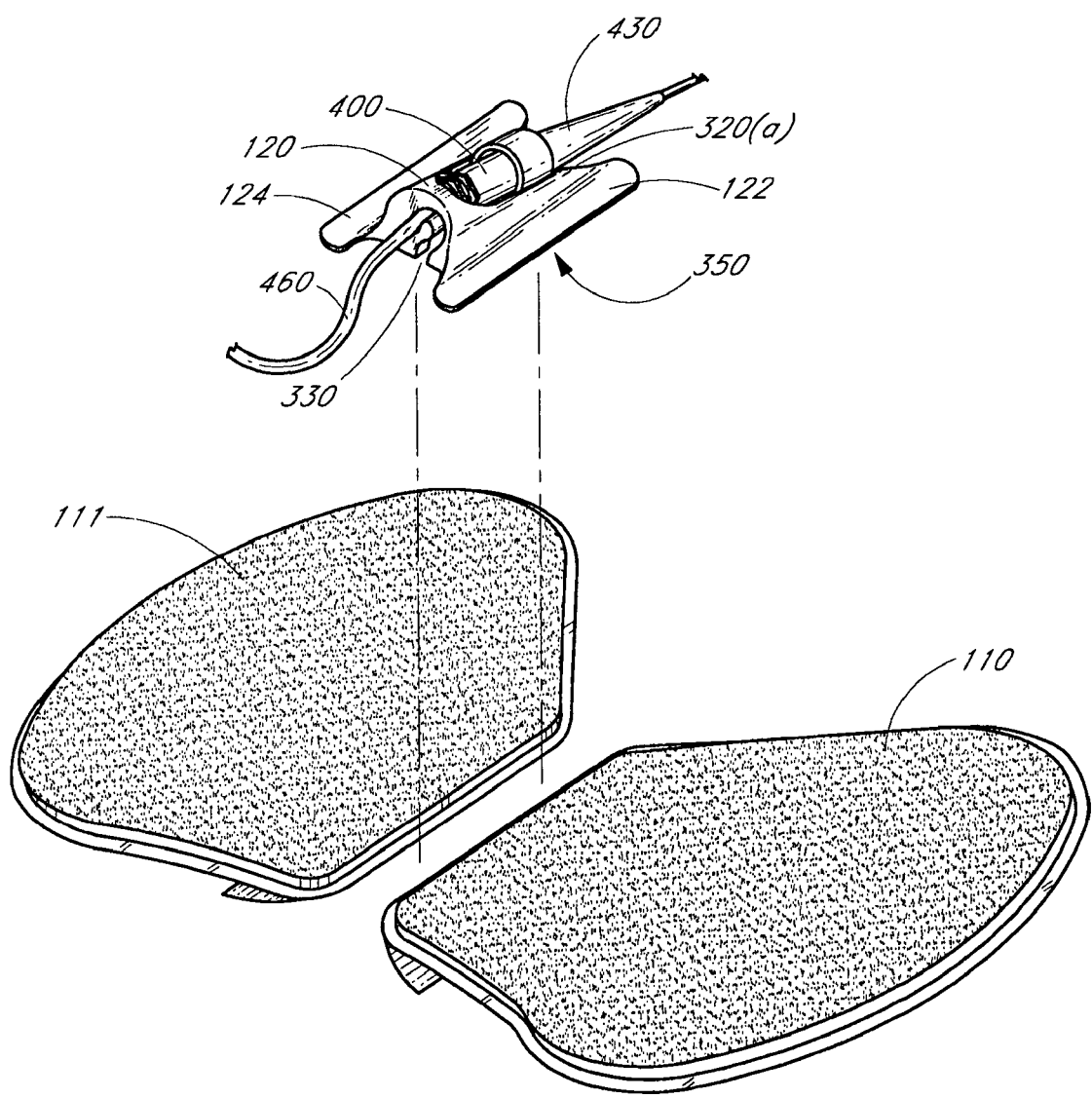
FIG. 7 is an exploded, perspective view of the connector fitting secured to the catheter hub of FIG. 4 and inserted into the retainer of FIG. 2, with the medical line being inserted into the hook-shaped slot of the retainer.
Figure 8:
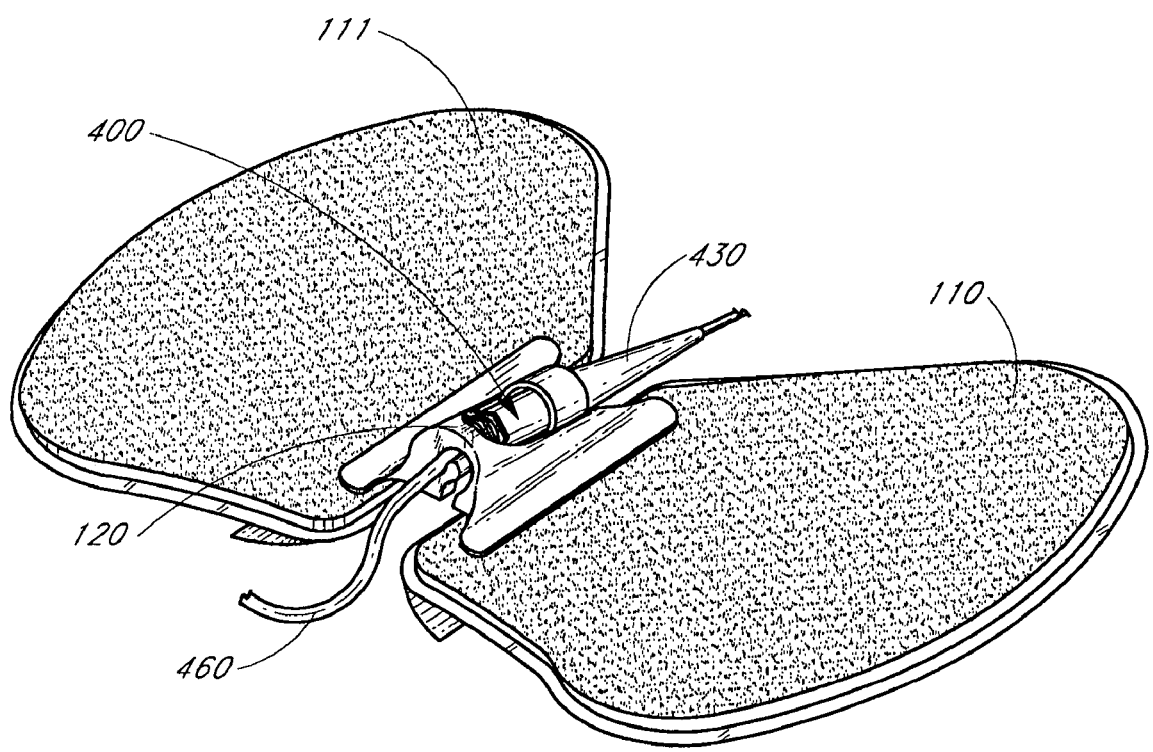
FIG. 8 is a perspective view of the connector fitting and catheter hub secured by the insertion site protection device of FIG. 1 with the medical line resting in the hook-shaped slot of the retainer.

Once a section of the medical article is captured within the retainer 120 (as shown in FIGS. 6, 7, and 8) the retainer at least restricts, if not prevents, lateral and transverse movement of the retained section of the medical article.

As shown most clearly in FIGS. 3C and 3D, the cradle portion 340 suitably extends for 180 degrees about the axis 397 and matches the size of the retained section of the medical article. The radial length of such an arc provides a degree of snap-fit securement between the cradle 340 and the secured portion of the medical line even without attaching the retainer 120 to the anchor pads 110, 111. In this way, the medical article can be placed in position prior to attaching the anchor pads 110, 111 to the skin of the patient without concern that the medical article will shift while the healthcare provider is attaching the insertion site protection device 100 to the patient. The cradle can extend for more than 180 degrees in order to more firmly grip the retained portion of the medical line.

The supports 320(a), 320(b) of the retainer 120 can include one or more grooves (not shown) or lateral projections in addition to the features described above. This can be advantageous when the medical article includes side extending members or reliefs. These grooves can extend circumferentially around the channel 360 and into the supports 320(a), 320(b) to thereby capture the radially extending member as the retained portion is inserted by the mounting wings 122, 124 and anchor pads 110, 111 and between the supports 320(a), 320(b).

Although certain features of the retainer 120 can be specifically configured for use with a medical line and connector fitting, it will be understood by those of skill in the art that such a retainer can be used with other medical lines or connector fitting as well. Furthermore, the retainers described herein can be modified to more effectively cooperate with various types of medical lines and connector fittings.

Connector Fitting

Figure 4:
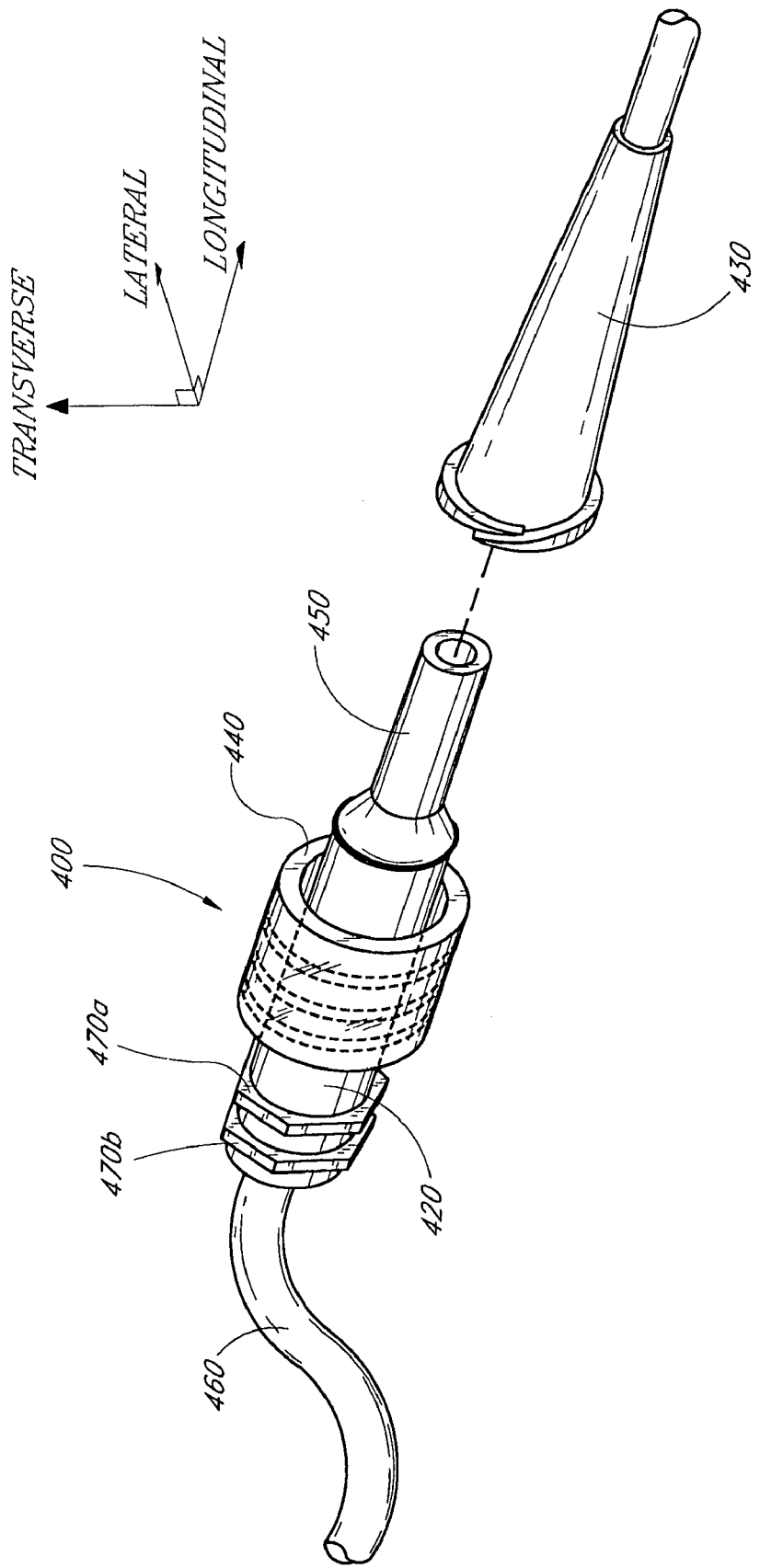
FIG. 4 is a perspective view of a catheter hub disassembled from a connector fitting.

An exemplary medical article for use with the embodiment of the insertion site protection device described above will now be described with reference to FIGS. 4 and 5. FIG. 4 is a perspective view of a catheter hub 430 and a connector fitting 400 with a spin nut 440, both for use with the retainer 120 of FIGS. 3A-3F. The connector fitting 400 is suitably disposed upon the end of a medical line 460 which can be connected to a drip bag, blood monitor, or other fluid related medical apparatus.

The connector fitting 400 comprises an elongated body 420 which is attached to the end of the medical line 460. The connector fitting 400 also comprises a portion which is desirably tapered along at least part of its longitudinal length so as to allow the end of this region to fit within the tapered conical portion of an adaptor 430. The tapered portion 450 of the connector fitting 400 also includes a centrally disposed lumen which communicates with the lumen of the medical line.

Figure 5:
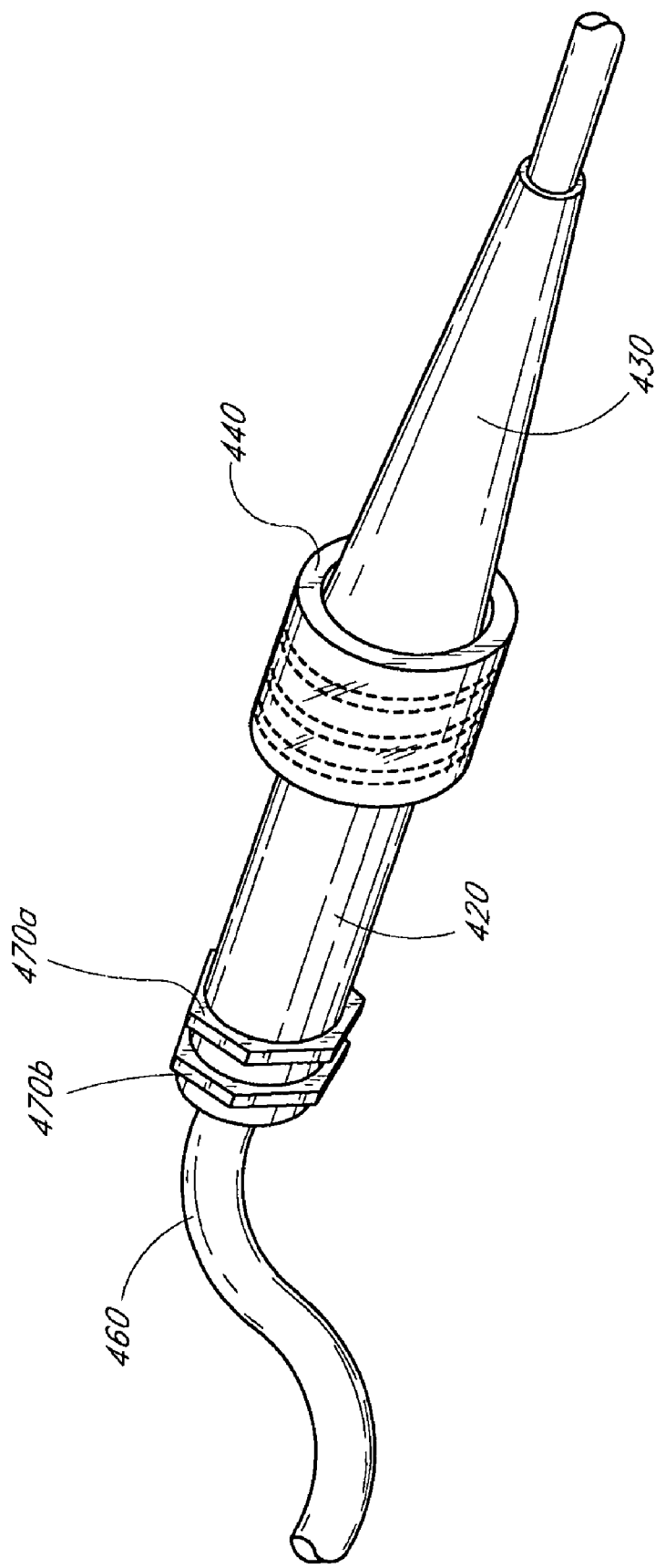
FIG. 5 is a perspective view of the connector fitting of FIG. 4 with a spin nut secured in the forward position and secured to the catheter hub.

FIG. 5 is a perspective view of the connector fitting 400 of FIG. 4 with the spin nut 440 secured in the forward position and secured to the catheter hub 430. When the connector fitting 400 is inserted into the adaptor 430, the lumen of the connector fitting is disposed in fluid communication with the lumen of the adaptor 430. This provides fluid communication between the medical line 460 and the patient.

As seen in FIGS. 4 and 5, the connector fitting 400 has at least one radially extending member 470(a) disposed upon an end of the elongated body 420 of the connector fitting 400 opposite the tapered end 450. It may be advantageous for the radially extending member 470(a) to extend completely around the circumference of the connector fitting 400. A second radially extending member 470(b) can also be disposed upon the elongated body 420, as can additional radial members (not shown). Those of skill in the art will recognize that the radially extending member or members need not have any particular shape or longitudinal thickness. Additionally, the radially extending members need not have the same shape. For instance, the first radially extending member 470(a) can have the hexagonal shape illustrated and the second radially extending member 470(b) can have a circular shape.

A spin nut 440 is disposed upon the connector fitting 400 around the elongated body 420 of the fitting. The spin nut 440 is substantially cylindrical in form and is able to move upon the connector fitting 400. The spin nut 440 is capable of both rotational motion around the axis of the connector fitting and axial motion in both the proximal and distal directions along the length of the elongated body 420 of the fitting. The spin nut 440 also includes internal screw threads which are illustrated with phantom lines in FIGS. 4 and 5. Depending on the relative longitudinal lengths of the retainer 120 and the connector fitting 400, the spin nut 440 may be located between the supports 320(a), 320(b) or beyond the ends of the supports 320(a), 320(b) in a proximal direction.

Adaptor

As seen in FIGS. 4 and 5, an adaptor 430 includes a body that, in the illustrated embodiment, is configured as a catheter hub and has a generally conical shape and tapers from a large radius to a smaller radius along its length. In the illustrated embodiment, the catheter adapter 430 comprises an external screw thread on the outside of the conical body near the end with the larger radius. The screw thread can be used in association with the spin nut 440 of the connector fitting 400 in order to securely interconnect the connector fitting 400 and the adaptor 430.

Operation

An exemplary process for installing a medical article into the insertion site protection device described above will now be described with reference to FIGS. 6 through 8. For ease of illustration, the anchor pads 110, 111 in FIGS. 7 and 8 are shown separated from the retainer 120. However, according to an aspect, the attachment of the retainer 120 to the anchor pads 110, 112 is performed during fabrication of the insertion site protection device 100 and not during use of the insertion site protection device 100 by the healthcare provider. The healthcare provider receives the anchor pads 110, 111 and the retainer as a unitary device. After the medical article is placed within the retainer 120, the healthcare provider simply attaches the anchor pads 110, 111 to the skin of the patient.

FIG. 6 is a perspective view of the connector fitting 400 secured to the catheter hub 430, both aligned with the anchor pads 110, 111 and the retainer 120. The healthcare provider can secure a medical line 460 and article to a patient using the above-described insertion site protection device 100 or a readily apparent modification thereof. The healthcare provider aligns the opening 350 located between the mounting wings 122, 124 of the retainer 120 over the connector fitting 400.

FIG. 7 is a perspective view of the connector fitting 400 secured to the catheter hub 430 and inserted into the retainer 120 with the medical line 460 being inserted into the hook-shaped slot 330 of the retainer 120. The lower opening 350 in the retainer 120 is guided over the connector fitting 400 whereby the connector fitting slides by the anchor pads 110, 111 and mounting wings 122, 124 and comes to rest between the supports 320(a), 320(b). Before, after, or contemporaneous with the insertion of the connector fitting into the retainer 120, the medical line 460 is guided through the hook-shaped slot 330 until the medical line is resting in the cradle portion 340 of the hook-shaped slot 330. Depending on the diameter of the medical line 460, a degree of snap-fit between the medical line 460 and the cradle portion 340 can be (although need not be) achieved. The retainer 120 is then slid proximally along the medical line 460 until a distal surface or protuberance of the connector fitting 400 contacts the proximal surface of the abutment wall 310. As can be seen, the body of the connector fitting 400 generally lies between the supports 320(a), 320(b) of the retainer 120 and adjacent to the abutment wall 310. The supports 320(a), 320(b) and the abutment wall 310 together will inhibit lateral movement and distal longitudinal migration of the medical article.

In the illustrated embodiment, the combination of the distance X between the supports 320(a), 320(b), the diameter and axial length of the cradle portion 340, the size and length Y of the channel 360, and the abutment wall 310 arrest movement of the retained section of the medical article in three dimension: longitudinally, laterally and transversely.

FIG. 8 is a perspective view of the retainer 120 attached to the anchor pads 110, 111 and securing the connector fitting 400 and catheter hub 430 therein. Once the connector fitting 400 or other medical article enters the lower opening 350 of the retainer 120 and the medical line 460 enters the access opening 399 and is guided to the cradle portion 340, the anchor pads 110, 111 are secured to the skin of the patient.

The healthcare provider can first remove the release liner 180 from the anchor pad 111 by gripping the pull tab 190 and pulling the liner 180 away from the lower surface 160 of the anchor pad 111. This exposes the adhesive layer of the anchor pad 111, which can then be applied to the skin of the patient near the site where the healthcare provider desires to secure the connector fitting 400 or other medical article. The release liner 182 for the anchor pad 110 is similarly removed and the anchor pad 110 is attached to the skin of the patient.

After the anchor pads 110, 111 are attached to the skin of the patient, the cover tape 130 is adhered to at least a portion of the exposed surfaces of the anchor pads 110, 111, the retained medical article, and the retainer 120. The cover tape 130 and the anchor pads 110, 111 form a clamshell around the medical article and retainer 120. In this way, the clamshell forms a sterile environment around the retained medical article and further arrests movement of the retained section of the medical article in three dimensions: longitudinally, laterally and transversely.

Additional Embodiments

Figure 9A:
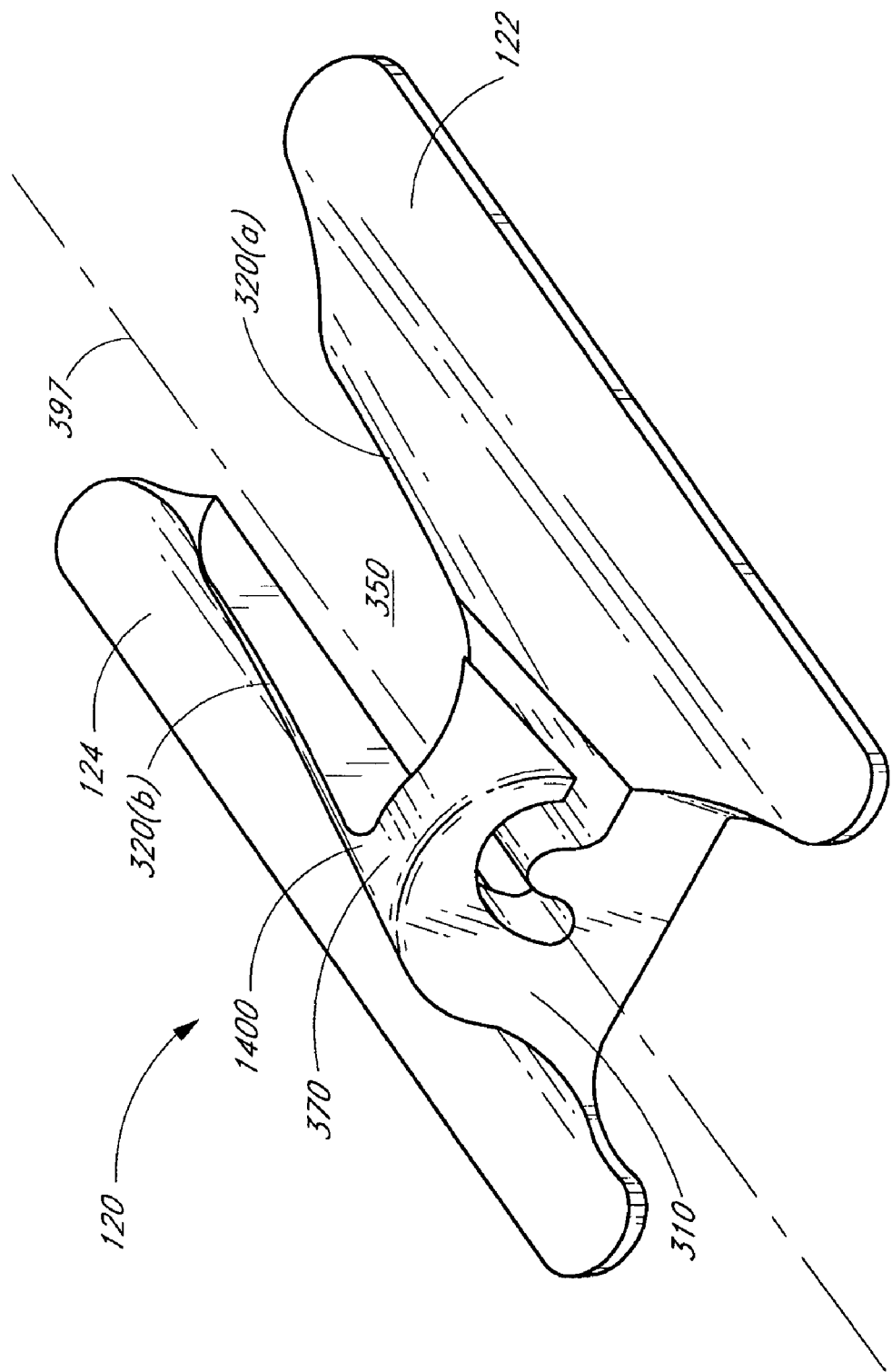
FIG. 9A is a perspective view of another embodiment of a retainer for use with the anchor pads of FIG. 2.

A retainer in accordance with another embodiment of the invention is illustrated in FIGS. 9A-9F, with FIG. 9A showing a perspective view of a retainer 120 for use with the anchor pads 110, 111 of FIG. 2. Only the body member 1400 of this embodiment differs from the above-described embodiment. Accordingly, the above description applies equally to the embodiment of FIGS. 9A-9F, unless otherwise indicated.

The body member 1400 illustrated in FIG. 9A-9F is configured to accept a medical line portion of a medical article in a lateral direction. A healthcare provider can install the medical article in the retainer 120 of FIGS. 9A-9F before or after the retainer 120 is attached to the skin of the patient. Body member 1400 further allows the healthcare provider to remove and replace the medical article without having to remove the retainer 120 from the skin of the patient. The embodiment of the retainer described with reference to FIGS. 3A-3F was configured to accept the medical line portion in an upward transverse direction.

FIG. 9B is a top plan view of the retainer 120 of FIG. 9A. FIG. 9C is a front side view of the retainer 120 of FIG. 9A and illustrates a horizontal, hook-shaped slot that receives a section of the medical article. As illustrated in FIGS. 9A, 9B, and 9C, the body member 1400 comprises an abutment wall 310, supports 320(a), 320(b) which extend in a longitudinal direction therefrom, and a web 370 which unites the supports 370(a), 370(b) at their bases. The open region located between the supports 320(a), 320(b) of the body member 1400 is aligned with the medical article. The medical article is inserted in a downward and transverse direction in between the supports 320(a), 320(b) such that at least a portion of the medical article is located between the supports 320(a), 320(b). The retainer 120 is then slid in a proximal direction relative to the medical article such that a contact surface of the medical article abuts against the proximal side of the abutment wall 310.

Before, after, or contemporaneous with inserting the medical article between the supports 320(a), 320(b), a section of the medical line 460 is laterally inserted through an access opening 399 and into a hook-shaped slot 330 in the abutment wall 310. The slot 330 guides the medical line 460 until the medical line 460 comes to rest in a cradle portion 340 at the terminus of the slot 330. Once in the cradle 340, the medical line 460 is inhibited from moving in a transverse and downward direction. The section of the medical line disposed within the cradle portion 340 is further inhibited from moving in a lateral direction. Movement of the medical article in a distal and longitudinal direction is inhibited by contact between the abutment wall 310 and a distal surface or protuberance of the medical article.

FIG. 9D is a back side view of the retainer 120 of FIG. 9A and illustrates a U-shaped channel 360 that receive a section of a connector fitting 400. The portion of the body member 1400 which is located proximal relative to the abutment wall 310, receives the catheter, adaptor, connector fitting, or other medical article. The medical article, such as a connector fitting 400 for a catheter, is inhibited from moving in a distal and longitudinal direction by the abutment wall 310. Additionally, features of the body member 1400, for example, the supports 320(a), 320(b) and the web 370, can further arrest motion of the medical article in lateral and transverse directions, respectively.

FIG. 9E is a side view of the retainer 120 of FIG. 9A. FIG. 9F is a bottom plan view of the retainer 120 of FIG. 9A. The base surfaces 380(a), 380(b) of the retainer 120 are secured to the mounting wings 122, 124. Positioning the connector fitting in the retainer 120 such that a distal surface or protuberance of the connector fitting contacts the abutment wall 310 inhibits longitudinal motion of the medical article and medical line portion of the medical article in a distal direction.

Figure 10A:
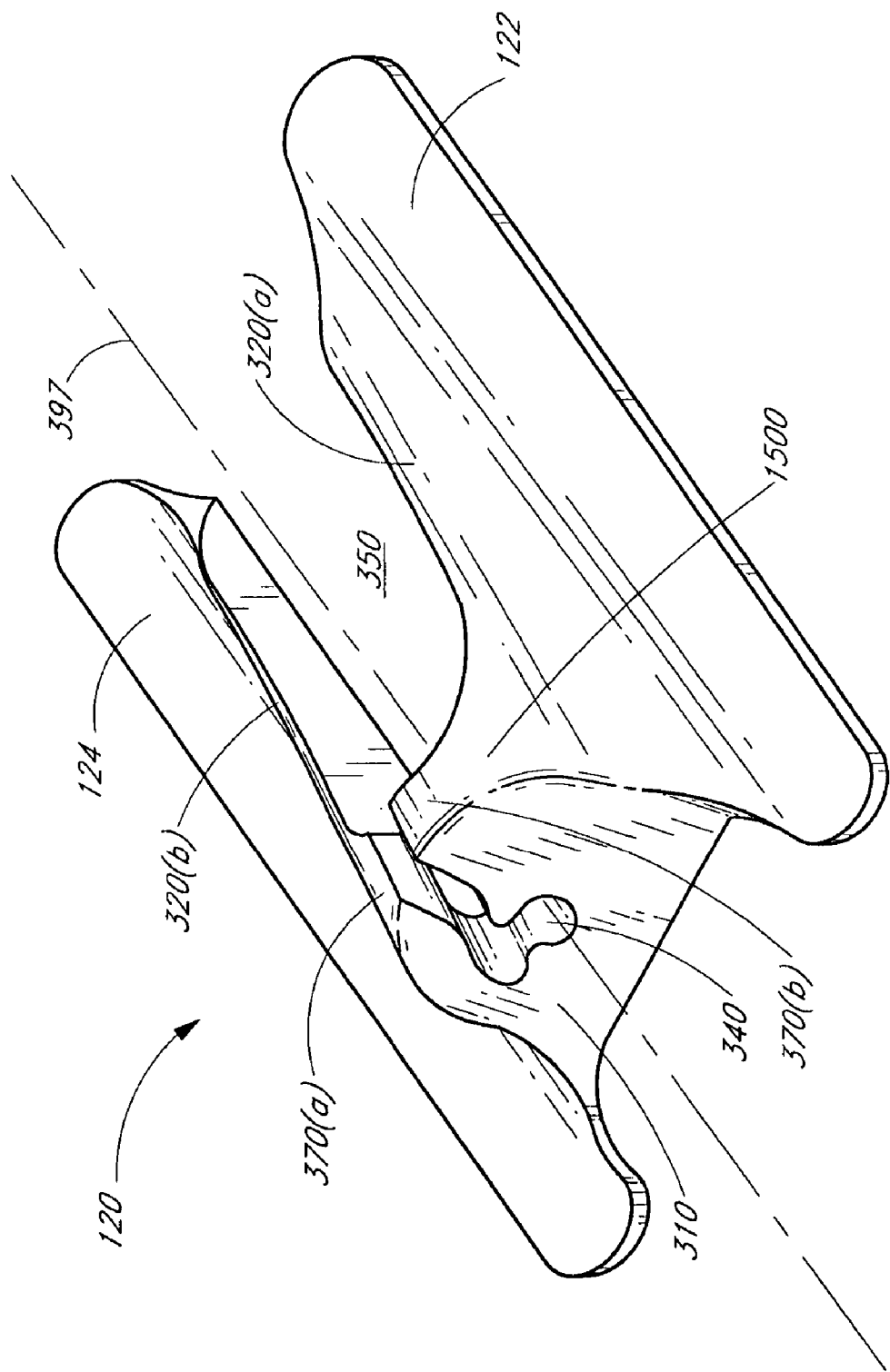
FIG. 10A is a perspective view of an additional embodiment of a retainer for use with the anchor pads of FIG. 2.

A retainer in accordance with another embodiment of the invention is illustrated in FIGS. 10A-10F, with FIG. 10A showing a perspective view of a retainer 120 for use with the mounting wings 122, 124 and anchor pads 110, 111 of FIG. 2. Only the body member 1500 of this embodiment differs from the embodiment illustrated in FIGS. 3A-3F. Accordingly, the above description applies equally to the embodiment of FIGS. 10A-10F, unless otherwise indicated.

The body member 1500 of the retainer 120 illustrated in FIGS. 10A-10F is configured to accept a medical line portion of a medical article in a transverse downward direction. A healthcare provider can install the medical article in the retainer 120 of FIGS. 10A-10F before or after the retainer 120 is attached to the skin of the patient. Body member 1500 further allows the healthcare provider to remove and replace the medical article without having to remove the retainer from the skin of the patient.

FIG. 10B is a top plan view of the retainer 120 of FIG. 10A. FIG. 10C is a front side view of the retainer 120 of FIG. 9A and illustrates a hook-shaped slot 330 that receives a section of a medical article. As illustrated in FIGS. 10A, 10B, and 10C, the body member 1500 comprises an abutment wall 310, supports 320(a), 320(b) which extend in a longitudinal direction therefrom, and a web 370 which extends between the supports 320(a), 320(b) at their bases. The web 370 for the third embodiment is separated into two adjacent webs 370(a), 370(b). For ease of description, the term web 370 is used for both portions. The channel 360 located between the supports 320(a), 320(b) of the body member 1500 is aligned with the medical article and attached medical line. The medical article is inserted in a downward and transverse direction in between the supports 320(a), 320(b) such that at least a portion of the medical article is located in the channel 360. The retainer 120 is then slid in a proximal direction relative to the medical article such that the proximal side of the abutment wall 310 abuts against a contact surface of the medical article.

Before, after, or contemporaneous with inserting the medical article into the opening 350, a section of the medical article is downwardly inserted through the access opening 399 and into the hook-shaped slot 330 in the abutment wall 310. The slot 330 guides the medical line 460 portion of the medical article through the slot 330 until the medical line 460 comes to rest in a cradle portion 340. Once in the cradle 340, the medical line 460 is inhibited from moving in a transverse and downward direction. The section of the medical line 460 is further inhibited from moving in a lateral direction. Movement of the medical article in a distal and longitudinal direction is inhibited by contact between the abutment wall 310 and a distal surface or protuberance of the medical article.

FIG. 10D is a back side view of the retainer 120 of FIG. 10A and illustrates a U-shaped channel 360 that receive a connector fitting portion of the medical article. The portion of the body member 1500 which is located proximal relative to the abutment wall 310, receives the catheter, adaptor, connector fitting, or other medical article. The medical article, such as a connector fitting for a catheter, is inhibited from moving in a distal and longitudinal direction by the abutment wall 310. Additionally, features of the body member 1500, for example, the supports 320(a), 320(b) and the web 370, can further arrest motion of the medical article in lateral and transverse directions, respectively.

FIG. 10E is a side view of the retainer 120 of FIG. 10A. FIG. 10F is a bottom plan view of the retainer 120 of FIG. 10A. The base surfaces 380(a), 380(b) of the mounting wings 122, 124 are secured to the anchor pads 110, 111. The positioning of the connector fitting in the retainer 120 such that a distal surface or protuberance of the connector fitting contacts the abutment wall 310 inhibits longitudinal motion of the medical article and integral medical line portion of the medical article in a distal direction.

The various embodiments of insertion site protection devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims.

What is claimed is:

1. A medical article securement system comprising:
   a medical article having a longitudinal axis;
   a medical line disposed upon an end of the medical article;
   at least one anchor pad including a lower adhesive surface configured to attach to a patient's skin; and
   a body member comprising,
      an abutment wall extending generally normal to the longitudinal axis,
      a slot in the abutment wall, the slot starting at an access opening and including a cradle, the slot being sized to pass at least a portion of the medical line between the access opening and the cradle, the cradle at least partially surrounding the medical line with a portion of the cradle being disposed between the secured medical line and the patient's skin,
      a first support and a second support disposed on the underside of the body member and generally on opposite sides of the longitudinal axis, the first support and the second support extend generally along the longitudinal axis and at least one of the first and second supports are attached to the at least one anchor pad,
      a web member extending between the first and second supports at a location near the abutment wall,
      an upper opening bounded by the web member and the upper edges of the first and second supports, the upper opening extending through the body member to a lower opening located between said first and second supports, and
      a receiving space generally defined on a proximal side of the abutment wall and between the first and second supports, at least a portion of the medical article being disposed above the upper opening at least when the medical article is received within the receiving space.

2. A medical article securement system as in claim 1, wherein the medical article comprises at least one contact surface which is configured to abut against the abutment wall to arrest movement of the medical article in at least one direction.

3. A medical article securement system as in claim 2, wherein the at least one contact surface comprises a surface of the medical article.

4. A medical article securement system as in claim 1, wherein the cradle is disposed so as to hold the retained portion of the medical article away from the patient's skin.

5. A medical article securement system as in claim 1, wherein the abutment wall inhibits longitudinal movement of the medical article in at least one direction.

6. A medical article securement system as in claim 5, wherein the surface of the medical article extends about the longitudinal axis of the medical article.

7. A medical article securement system as in claim 1, additionally comprising a second anchor pad supporting the body member and ingress into the slot is achieved by passing at least a portion of the medical article between the anchor pads.

8. A medical article securement system as in claim 1, wherein the access opening into the slot is located on a lower side of the abutment wall.

9. A medical article securement system as in claim 1, wherein the access opening is located on an upper side of the abutment wall.

10. A medical article securement system as in claim 1, wherein the access opening is located on a side of the abutment wall.

11. A medical article securement system as in claim 1, wherein the at least one support includes a first mounting wing coupled to the body member and attached to the at least one anchor pad.

12. A medical article securement system as in claim 1 additionally comprising an adhesive, the adhesive adhering to the medical article when the medical article is inserted into the cradle.

13. A medical article securement system as in claim 1, wherein a portion of the body member is transparent.

14. A medical article securement system as in claim 1, wherein the slot has an inverted, hook-shape.

15. A medical article securement system as in claim 1, wherein a surface defined by the upper opening has a curvilinear shape.

16. A medical article securement system as in claim 1, wherein a surface defined by the upper opening passes through the medical article at least when the medical article is received within the receiving space.

17. A securement system comprising:
a medical article having a longitudinal axis;
a medical line disposed upon an end of the medical article;
at least one anchor pad including a lower adhesive surface configured to attach to a patient's skin; and
a body member comprising,
an abutment wall extending generally normal to the longitudinal axis,
a slot having an access opening and a cradle, the slot being sized to pass the retained portion of the medical line therebetween, the cradle at least partially surrounding the medical line with a portion of the cradle being disposed between the secured medical line and the patient's skin, the access opening being disposed on the body member to allow at least ingress of the portion of the medical article into the slot,
a first support and a second support disposed on the underside of the body member and generally on opposite sides of the longitudinal axis, the first support and the second support extending generally along the longitudinal axis and being attached to the at least one anchor pad,
a web member extending between the first and second supports at a location near the abutment wall,
an upper opening bounded by the web member and the upper edges of the first and second supports, the upper opening extending through the body member to a lower opening located between said first and second supports, and
a receiving space generally disposed on a proximal side of the abutment wall and between the first and second supports, at least a portion of the medical article being disposed above the upper opening at least when the medical article is received within the receiving space.

18. A securement system as in claim 17, additionally comprising a second anchor pad supporting the body member and ingress into the slot is achieved by passing at least a portion of the medical article between the anchor pads.

19. A securement system as in claim 17, wherein the access opening into the slot is located on a lower side of the abutment wall.

20. A securement system as in claim 17, wherein the access opening into the slot is located on a lower side of the body member.

21. A securement system as in claim 17, wherein the slot has an inverted, hook-shape.

22. A securement system as in claim 17, wherein the slot has a serpentine shape.

* * * * *